(12) United States Patent
Zhou et al.

(10) Patent No.: US 9,102,695 B2
(45) Date of Patent: Aug. 11, 2015

(54) PHOSPHINIC ACIDS AND THEIR SULFUR DERIVATIVES AND METHODS FOR THEIR PREPARATION

(71) Applicant: Cytec Technology Corp., Wilmington, DE (US)

(72) Inventors: Yuehui Zhou, Changshu (CN); Jeffrey Charles Henry Dyck, Niagara on the Lake (CA); Boban Jakovljevic, Niagara Falls (CA); Cyril Christian Henri Bourget, Cholet (FR); Allan James Robertson, Thorold (CA); Donato Nucciarone, Stoney Creek (CA)

(73) Assignee: CYTEC TECHNOLOGY CORP., Wilmington, DE (US)

( * ) Notice: Subject to any disclaimer, the term of this patent is extended or adjusted under 35 U.S.C. 154(b) by 0 days.

(21) Appl. No.: 14/286,254

(22) Filed: May 23, 2014

(65) Prior Publication Data

US 2014/0275615 A1    Sep. 18, 2014

Related U.S. Application Data

(62) Division of application No. 12/304,484, filed as application No. PCT/CA2007/001043 on Jun. 12, 2007, now Pat. No. 8,764,880.

(30) Foreign Application Priority Data

Jun. 14, 2006 (CA) .................................... 2550557

(51) Int. Cl.
| | | |
|---|---|---|
| *C07F 9/30* | (2006.01) | |
| *C07F 9/02* | (2006.01) | |
| *C07F 9/28* | (2006.01) | |
| *C22B 5/00* | (2006.01) | |
| *C22B 17/00* | (2006.01) | |
| *C22B 19/00* | (2006.01) | |
| *C22B 47/00* | (2006.01) | |
| *C07F 9/50* | (2006.01) | |

(52) U.S. Cl.
CPC ............... *C07F 9/301* (2013.01); *C07F 9/5004* (2013.01); *C07F 9/5059* (2013.01)

(58) Field of Classification Search
None
See application file for complete search history.

(56) References Cited

U.S. PATENT DOCUMENTS

| 2,584,112 | A | | 2/1952 | Brown |
|---|---|---|---|---|
| 4,348,367 | A | | 9/1982 | Rickelton et al. |
| 4,353,883 | A | | 10/1982 | Rickelton et al. |
| 4,374,780 | A | | 2/1983 | Robertson |
| 4,555,368 | A | | 11/1985 | Robertson |
| 4,721,605 | A | | 1/1988 | Brown et al. |
| 5,028,403 | A | * | 7/1991 | Rickelton et al. ............... 423/24 |
| 5,925,784 | A | | 7/1999 | Sugiya et al. |

FOREIGN PATENT DOCUMENTS

| EP | 0236542 B1 | 6/1992 |
|---|---|---|
| GB | 902802 | 8/1962 |

OTHER PUBLICATIONS

Tait, "Cobalt-nickel separation: The extraction of cobalt (II) and nickel (II) by Cyanex 301, Cyanex 302 and Cyanex 272" Hydrometallurgy, 1993, pp. 365-372, 32.
Rickelton et al., "Solvent extraction with organophosphines—Commercial and potential applications" Separation Science and Technology, 1988, pp. 1227-1250, 23(12&13).
Xun et al., "Solvent extraction of cobalt and nickel in bis(2,4,4-trimethylpentyl) phosphinic acid, Cyanex 272" Solvent Extraction and Ion Exchange, 187, pp. 205-226, 5(2).
International Search Report for PCT/CA2007/001043; mailed Sep. 27, 2007.
Written Opinion for PCT/CA2007/001043; mailed Sep. 27, 2007.

* cited by examiner

*Primary Examiner* — Yun Qian
(74) *Attorney, Agent, or Firm* — Charles E. Bell

(57) ABSTRACT

Methods of preparing compounds according to Formula (I):

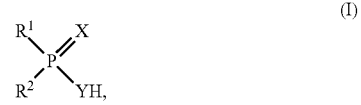

and salts thereof as well as their corresponding phosphine intermediates are provided herein, wherein $R^1$ and $R^2$ are different and each of $R^1$ and $R^2$ is independently selected from an organic radical that branches at the alpha carbon and an organic radical that branches at the beta carbon, and each of X and Y is independently O or S, and wherein said compound is a liquid at room temperature.

9 Claims, No Drawings

PHOSPHINIC ACIDS AND THEIR SULFUR DERIVATIVES AND METHODS FOR THEIR PREPARATION

CROSS-REFERENCE TO RELATED APPLICATIONS

This application is a divisional of U.S. application Ser. No. 12/304,484, filed Dec. 12, 2008 (allowed), which is the U.S. National Phase application of International Application No. PCT/CA2007/001043, filed Jun. 12, 2007 (expired) and published as WO 2007/143832, which claims priority to Canadian Application No. 2,550,557, filed Jun. 14, 2006 (granted), each of which is incorporated by reference herein in its entirety.

FIELD OF THE INVENTION

The present invention relates generally to the field of organic chemistry. More particularly, the present invention provides novel organic phosphinic acids and their sulfur derivatives and methods for their preparation. These novel compounds find utility as metal extractants.

SUMMARY OF THE INVENTION

In one aspect, the invention provides a compound defined by formula (I):

wherein:

$R^1$ and $R^2$ are different and each of $R^1$ and $R^2$ is independently selected from:

(a) —$CH_2$—$CHR^3R^4$, where $R^3$ is methyl or ethyl; and $R^4$ is an optionally substituted alkyl or heteroalkyl; and (b) —$CR^3(CH_2R^5)R^6$, where $R^3$ is methyl or ethyl; and $R^5$ is H or an optionally substituted alkyl or heteroalkyl, and $R^6$ is an optionally substituted alkyl or heteroalkyl; or $R^5$, $R^6$ and the ethylene group to which they are bonded form a five or six-membered optionally substituted cycloalkyl or heterocycloalkyl ring;

and each of X and Y is independently O or S.

Thus, in embodiments, the invention provides the following compounds of formula (I):

(a) (2,4,4-trimethylpentyl)(1,1,3,3-tetramethylbutyl)phosphinic acid;

(b) (1,1,3,3-tetramethylbutyl)(2-ethylhexyl)phosphinic acid;

(c) (2,4,4-trimethylpentyl)(2-ethylhexyl)phosphinic acid;

(d) (2,4,4-trimethylpentyl)(1-methyl-1-ethylpentyl)phosphinic acid; and (e) (1-methyl-1-ethylpentyl)(2-ethylhexyl)phosphinic acid;

and their mono- and dithio-derivatives, and salts thereof.

As described herein, compounds of formula (I) can be prepared for example by allowing a secondary phosphine of formula (II):

to react with (i) an oxidizing agent, to produce the corresponding phosphinic acid; (ii) sulfur, to produce the corresponding dithiophosphinic acid; or (iii) a limited amount of oxidizing agent, to produce the corresponding phosphine oxide, which is subsequently allowed to react with sulfur to produce the corresponding monothiophosphinic acid.

In another aspect, the present invention provides a method for preparing a secondary phosphine of formula (II) wherein $R^1$ and $R^2$ are as defined above and $R^2$ is —$CH_2$—$CHR^3R^4$, wherein the method comprises allowing a primary phosphine of formula $R^1PH_2$ to react with an olefin of formula $CH_2$=$CR^3R^4$ under free radical conditions.

In another aspect, the present invention provides a method for preparing a secondary phosphine of formula (II) wherein $R^1$ and $R^2$ are as defined above and $R^2$ is —$CR^3(CH_2R^5)R^6$, wherein the method comprises allowing a primary phosphine of formula $R^1PH_2$ to react in the presence of an acid catalyst with an olefin of formula $HR^5C$=$CR^3R^6$.

Some of the secondary phosphine compounds of formula (II) are novel. Thus, in embodiments, the invention provides the following secondary phosphine compounds:

(a) (2,4,4-trimethylpentyl)(1,1,3,3-tetramethylbutyl)phosphine;

(b) (1,1,3,3-tetramethylbutyl)(2-ethylhexyl)phosphine;

(c) (2,4,4-trimethylpentyl)(2-ethylhexyl)phosphine;

(d) (2,4,4-trimethylpentyl)(1-methyl-1-ethylpentyl)phosphine; and (e) (1-methy-1-ethylpentyl)(2-ethylhexyl)phosphine.

In another aspect, the present invention provides use of a compound of formula (I) or a salt thereof as a metal extractant.

In another aspect, the invention provides a process for the extraction of a metal from a metal-bearing solution, comprising contacting said solution with a compound of formula (I), allowing the compound of formula (I) to form a complex with the metal, and recovering the complex. In embodiments, a compound of formula (I) in which X and Y are both O, or a salt thereof, can be used to selectively extract cobalt(II) from an aqueous solution comprising cobalt(II) and nickel(II).

DETAILED DESCRIPTION OF CERTAIN EMBODIMENTS OF THE INVENTION

Values for $R^1$ and $R^2$ are chosen to yield compounds of formula (I) that have low melting points. For many applications, the compound of formula (I) is used in its liquid state. Accordingly, compounds of formula (I) that are liquid at room temperature (e.g. over a temperature range of between about 15° C. to about 25° C., more particularly at a temperature of about 15° C., about 20° C. and about 25° C.) are generally suitable for applications that are carried out at or near room temperature, whereas compounds of formula (I) that melt at low temperature (for example at temperatures less than about 30° C., about 40° C., about 50° C., about 60° C., about 80° C., about 100° C., about 150° C.) are generally suitable for applications that are carried out at slightly elevated temperatures (i.e. above the melting point of the compound of formula (I)). Hence, values for $R^1$ and $R^2$ are chosen such that $R^1$ and $R^2$ are different, as the resulting asymmetry tends to decrease the melting point of the compound.

Branching is another determinant of melting point. Specifically, the melting point tends to decrease as the degree of branching of $R^1$ and $R^2$ increases. By definition, each of $R^1$ and $R^2$ is independently branched at the alpha or beta carbon, but additional branching can occur at the alpha or omega carbon or at any intermediate point. Branching at the alpha carbon and/or beta carbon may improve the ability of an organophosphinic acid to bind cobalt selectively over nickel and/or calcium, by increasing steric hindrance around the central phosphorus atom and thus favouring coordination of the phosphinic acid with cobalt(II).

The presence of one or more chiral centres in $R^1$ and $R^2$ tends to decrease the melting point, by providing a mixture of stereoisomers.

The melting point tends to increase as the number of carbon atoms in the compound increases, so $R^1$ and $R^2$ are typically chosen such that the compound of formula (I) contains no more than about 20 carbon atoms. However, for some purposes (such as metal extraction from aqueous solutions), compounds of formula (I) that are hydrophobic or "water immiscible" are desired. The term "water immiscible" is intended to describe compounds that form a two phase system when mixed with water, but does not exclude compounds that dissolve in water nor compounds that dissolve water, provided that the two phase system forms. For these purposes, compounds of formula (I) that have a total of about 12 carbon atoms or more can be useful.

For many applications (such as metal extraction applications), $R^1$ and $R^2$ are chosen to yield compounds that are miscible (preferably in all proportions) with an organic solvent used in the particular application. The miscibility of compounds of formula (I) in the specified organic solvent can readily be determined (e.g. by eye), without the exercise of inventive skill.

$R^1$ and $R^2$ can contain heteroatoms (e.g. the carbon backbone can be interrupted by one or more atoms selected from N, O, and S) or bear additional substituents (such as hydroxyl, halo, alkoxy, alkylthio, carboxy, and acetyl groups), provided that the substituents or heteroatoms do not interfere with the preparation or utility of the compounds of the invention, as can readily be determined by routine experimentation requiring no inventive skill. However, the presence of heteroatoms and additional substituents are likely to increase costs. Therefore, for many purposes, $R^1$ and $R^2$ will not contain heteroatoms or bear additional substituents.

Thus, for many purposes, each of $R^1$ and $R^2$ is independently an alkyl group or cycloalkyl group made up of hydrogen and carbon atoms only, such as: a $C_5$-$C_{16}$ alkyl group, i.e. an alkyl group that has a total of between 5 and 16 carbon atoms (i.e. 5, 6, 7, 8, 9, 10, 11, 12, 13, 14, 15, or 16 carbon atoms) and often between 6 to 10 carbon atoms; or a $C_5$-$C_{16}$ cycloalkyl group, e.g. a five- or six-membered ring substituted with at least one alkyl group (i.e. $R^3$ and optionally one or more additional alkyl groups), such that said cycloalkyl group has a total of between 6 and 16 carbon atoms (i.e. 6, 7, 8, 9, 10, 11, 12, 13, 14, 15, or 16) and often between 6 to 10 carbon atoms. Herein, the term "alkyl" includes straight and branched chain alkyl radicals.

$R^3$, $R^4$, $R^5$ and $R^6$ are chosen to provide the desired values for $R^1$ and $R^2$. For example, when $R^1$ is a $C_5$-$C_{16}$ alkyl of formula —$CR^3(CH_2R^5)R^6$ and $R^3$ and $R^5$ are both methyl, then $R^6$ is $C_1$-$C_{12}$ alkyl. $R^4$, $R^5$ and $R^6$ may be branched.

Thus, suitable values for $R^1$ and $R^2$ include: 2,4,4-trimethylpentyl; 1,1,3,3-tetramethylbutyl; 2-ethylhexyl; and 1-methyl-1-ethylpentyl.

(I) Methods for Preparing Compounds of Formula (I):

Compounds of formula (I) can be prepared using known chemical reactions. For example, a secondary phosphine of formula (II)

(II)

wherein $R^1$ and $R^2$ are as defined above, can be prepared by adding a primary phosphine to an olefin either by way of acid-catalysed addition or under free radical conditions. Then, the secondary phosphine can be reacted with: (i) an oxidizing agent, to produce phosphinic acid; (ii) sulfur, to produce dithiophosphinic acid; or (iii) a limited amount of oxidizing agent, to produce a phosphine oxide that can subsequently be allowed to react with sulfur to prepare monothiophosphinic acid.

Free radical conditions are useful for preparing a secondary phosphine that has an R group substituted at the beta carbon atom, because free radical conditions favour addition of phosphine to a primary carbon atom, such as the terminal carbon atom of a 1-alkene.

Acid catalysis is useful for preparing a secondary phosphine that has an R group substituted at the alpha carbon, because acid catalysis favours addition of the phosphine to a tertiary carbon.

(A) Preparation of Secondary Phosphines Under Free Radical Conditions

Methods for adding phosphines to olefins under free radical conditions are known. For example, U.S. Pat. No. 4,374,780 describes a method for making bis(2,4,4-trimethylpentyl)phosphinic acid by free radical addition of two moles of 2,4,4-trimethylpentene-1 to phosphine followed by oxidation with hydrogen peroxide.

Thus, a method for preparing a secondary phosphine of formula (II):

(II)

wherein $R^1$ and $R^2$ are as defined above and $R^2$ is —$CH_2$—$CHR^3R^4$, comprises, for example, allowing a primary phosphine of formula $R^1PH_2$ to react with an olefin of formula $CH_2$=$CR^3R^4$ under free radical conditions.

Free radical initiators are known in the art and the skilled person will be able to select a suitable free radical initiator for use in the above-described reaction. Mention is made of azobis free radical initiators, such as azobisisobutylnitrile.

The phosphine addition reaction is not particularly temperature limited and will take place over a wide range of temperatures. Consequently, a temperature range for carrying out the reaction is generally chosen based on the half life of the initiator employed. For example, for azobisisobutylnitrile, the reaction can be carried out at temperatures ranging from about 40° to about 110° C., preferably about 60° to about 90° C.

To reduce the production of unwanted tertiary phosphines, the reaction should be carried out with a molar excess of primary phosphine.

For example, (2,4,4-trimethylpentyl)(2-ethylhexyl)phosphine can be prepared by addition of:
(a) (2,4,4-trimethylpentyl)phosphine to 2-ethylhex-1-ene or
(b) 2-ethylhexylphosphine to (2,4,4-trimethyl)pentene-1 under free radical conditions as described above.

(B) Preparation of Secondary Phosphines by Acid-Catalyzed Addition

Methods for adding phosphines to olefins via acid catalyzed addition have been known for some time (see for example U.S. Pat. No. 2,584,112). For example, U.S. Pat. No. 5,925,784 describes a method of making bis(1,1,3,3-tetramethylbutyl)phosphinic acid by acid-catalyzed addition of phosphine to diisobutylene, followed by oxidation with hydrogen peroxide.

Thus, a method for preparing a secondary phosphine of formula (II):

wherein $R^1$ and $R^2$ are as defined above and $R^2$ is —$CR^3(CH_2R^5)R^6$, comprises, for example, allowing a primary phosphine of formula $R^1PH_2$ to react in the presence of an acid catalyst with an olefin of formula $HR^5C=CR^3R^6$.

The acid catalysed addition step can be conveniently carried out in the presence of a protonatable organic solvent (i.e. an organic solvent that contains a hydroxy (OH) group), such as a glycol or glycol ether. Examples of suitable glycol or glycol ethers for this purpose include: ethylene glycol, glycerine, and glyme.

The acid catalyst can be any strong non-oxidizing acid. Alkylsulfonic acids (including but not limited to methanesulfonic acid and toluenesulfonic acid) are preferred due to their availability, low cost and compatibility with most stainless steels (which are commonly used to make industrial reactors). However, other strong non-oxidizing acids such as HCl and $H_3PO_4$ may be used in the method of the invention, although HCl will require that the reaction be carried out in a halide resistant reactor. The molar ratio of acid catalyst to primary phosphine is about 1:1 to about 5:1, preferably about 1.5:1.0. A molar excess of acid catalyst may improve yield, but increases the cost of the process.

In general, the acid-catalyzed addition step can be carried out by adding the acid catalyst to a vessel containing the primary phosphine and the olefin under an inert atmosphere (such as nitrogen) at atmospheric pressure and elevated temperature (e.g. about 50° to about 160° C., preferably about 75° to about 125° C.), and allowing the reaction to proceed for between about 2 to about 88 hours (preferably between about 8 to about 20 hours). Elevated temperatures may improve yield and reduce reaction time. The reaction product(s) can be analyzed using standard methods, e.g. gas chromatography (GC) and/or nuclear magnetic resonance (NMR) analysis.

The presence of an excess of olefin may improve yield in the phosphine addition step but can lead to olefin dimers and trimers. The alkylphosphine may be present in excess, but the excess alkylphosphine should typically be removed prior to oxidation. Therefore, in most cases, the reaction will comprise olefin and the primary phosphine in a molar ratio ranging from about 0.5:1 to about 3:1, preferably about 1.5:1.0.

Upon completion of the acid catalysed addition step, the reaction mixture can be worked up (e.g. by washing with aqueous base, recovering the organic phase, and removing any unreacted starting materials and solvent under vacuum at elevated temperature (e.g. about 80° C.)), to provide a crude secondary phosphine preparation that can be used directly in the oxidation step, without further purification.

The olefin can be a single species or a mixture of two related olefin species, each having a tertiary carbon double-bonded to a neighbouring carbon atom. For example, diisobutylene is ordinarily available commercially as a mixture of (2,4,4-trimethyl)pentene-1 and (2,4,4-trimethyl) pentene-2. In the presence of an acid catalyst, a primary phosphine can add to both of these species of olefin at their beta carbon, which is tertiary.

For example:
(a) (2,4,4-trimethylpentyl)(1,1,3,3-tetramethyl)phosphine can be prepared by allowing (2,4,4-trimethylpentyl)phosphine to react with diisobutylene in the presence of an acid catalyst;
(b) (1,1,3,3-tetramethylbutyl)(2-ethylhexyl)phosphine can be prepared by allowing 2-ethylhexylphosphine to react with diisobutylene in the presence of an acid catalyst;
(c) (2,4,4-trimethylpentyl)(1-methyl-1-ethylpentyl)phosphine can be prepared by allowing (2,4,4-trimethyl-pentyl) phosphine to react with 2-ethylhexene-1 in the presence of an acid catalyst; and
(d) (1-methyl-1-ethylpentyl)(2-ethylhexyl)phosphine can be prepared by allowing 2-ethylhexylphosphine to react with 2-ethylhexene-1 in the presence of an acid catalyst.

(C) Oxidation of a Secondary Phosphine

The secondary phosphines described above can be oxidized to prepare the corresponding phosphinic acids.

At a molecular level, the oxidation of the secondary phosphine occurs in two steps. First, the secondary phosphine is oxidized to phosphine oxide, which is then oxidized to form the phosphinic acid. In practice, complete oxidation of the secondary phosphine can be accomplished in a single reaction. The secondary phosphine can be oxidized, for example, by allowing it to react with an oxidizing agent (preferably hydrogen peroxide) in the presence of an acid catalyst (e.g. sulfuric acid) and water, at atmospheric pressure and elevated temperature (e.g. about 50° C. to about 110° C., preferably about 80° C. to about 100° C.) for about 4 to about 16 hours or until complete. Lower temperatures slow the reaction, resulting in longer reaction times. However, higher temperatures tend to remove one alkyl group, resulting in the formation of some monoalkylphosphonic acid side product. The course of the reaction can be followed for example by $^{31}P$ NMR.

Suitable oxidizing agents include hydrogen peroxide, which is an inexpensive and convenient oxidizing agent. The stoichiometry of the oxidation reaction dictates that two equivalents of hydrogen peroxide react with one equivalent of phosphine in this reaction. However, the presence of an excess of hydrogen peroxide can improve yield (i.e. pushing the oxidation reaction towards completion) at little extra cost. So in many cases, hydrogen peroxide will be present in excess of the secondary phosphine, say in a ratio of equivalents ranging from between about 2:1 to about 4:1, preferably about 3:1.

Upon completion of the reaction, the reaction mixture can be worked up (e.g. by washing with aqueous base (e.g.

sodium hydroxide) then aqueous acid (e.g. sulfuric acid), then drying under vacuum at elevated temperature (e.g. about 80° C.)), to afford a liquid product that contains the desired phosphinic acid product.

The foregoing method generally affords a liquid end product that contains the desired phosphinic acid, as well as certain side products. When the process is carried out under suitable conditions, the desired phosphinic acid product can be the major component (e.g. 80-95% or more by weight) of the liquid end product.

The liquid end product of the prescribed method can be used in metal extraction processes without further purification, as most of the side products are not expected to interfere with the metal extraction process. However, the oxidation step can result in the production of phosphonic acid side products (i.e. $R^1PO(OH)_2$ and $R^2PO(OH)_2$), which may for example reduce the selectivity of the end product for cobalt over calcium and nickel. If desired, reaction conditions (especially temperature, as noted above) can be chosen to minimize the production of phosphonic acid side products. If desired, the liquid end product can be washed with one or more alkaline water washes to reduce the level of monophosphonic acids to an acceptable level, e.g. about 1% or less.

(D) Reaction of Secondary Phosphines or Phosphine Oxides with Sulfur

The secondary phosphines described above can also be used as intermediates to prepare the corresponding monothiophosphinic acids and dithiophosphinic acids.

Dithiophosphinic acids can be prepared, for example, by allowing a secondary phosphine to react with sulfur, in accordance with known methods (e.g. as described in U.S. Pat. No. 5,925,784 or GB902802). Secondary phosphines just defined can be reacted with sulfur, water, and a base reagent, such as ammonium hydroxide, to produce the salt of the corresponding secondary dithiophosphinic acid, such as the ammonium salt thereof. Reactions of this type are generally carried out at temperatures in the range of about 0° C. to about 100° C., preferably about 15° C. to about 75° C. The salt thus prepared can be reacted with an acid, such as HCl, dilute sulfuric acid, or methane sulfonic acid to produce the secondary dithiophosphinic acid. These reactions generally are made to take place at temperatures in the range of about −30° C. to about 75° C., preferably about 10° C. to about 50° C.

Monothiophosphinic acids can be prepared, for example, by:
(i) allowing a secondary phosphine to react with a limiting amount of an oxidizing agent, to produce a secondary phosphine oxide; and
(ii) allowing the secondary phosphine oxide to react with sulfur to produce a monothiophosphinic acid.

A suitable method for preparing monothiophosphinic acids is described in for example U.S. Pat. No. 4,555,368. Briefly, the secondary phosphine can be oxidized to form the corresponding diorganophosphine oxide, without forming significant amounts of the corresponding diorganophosphinic acid. To achieve this, the oxidation reaction can be performed by gradual or incremental addition of the oxidizing agent at a rate which provides a controlled temperature of from about 40° C. to about 60°, and preferably from about 50° C. to about 55° C. The amount of oxidizing agent added should be sufficient to oxidize substantially all of the secondary phosphine and generally an equimolar amount of oxidizing agent is used. The time of addition may vary depending on the starting amounts of secondary phosphine used. Generally, oxidation under controlled temperature conditions can be completed with gradual or incremental addition of the oxidizing agent over a period of from about 1 to about 3 hours.

The selection of a particular oxidizing agent is not critical, so long as it is effective to oxidize the secondary phosphine to the secondary phosphine oxide. Hydrogen peroxide is the preferred oxidizing agent for use herein, because it is inexpensive, readily available, and the temperature and rate of the oxidation reaction are easily controlled with its use.

After substantially all of the secondary phosphine has been converted to the corresponding secondary phosphine oxide, the resulting secondary phosphine can be heated to an elevated temperature of between about 60° C. to about 90° C., and preferably from about 65° C. to about 75° C., and an excess of sulfur and excess of an hydroxide compound added to convert the secondary phosphine oxide to the corresponding monothiophosphinate compound. The sulfurization reaction in the presence of base can be conducted at temperatures of between about 60° C. to about 90° C., and allowed to proceed substantially to completion. Generally, the reaction can be completed within a period of from about 1 to about 5 hours at temperatures of 60° C. to 90° C.

The resulting monothiophosphinic acid can undergo tautomerization, interconverting between the following tautomers;

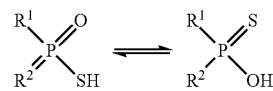

(II) Utility of Compounds of Formula I

It is known in the art that organic phosphinic acids can be used for metal extraction, notably cobalt (II) extraction (see for example U.S. Pat. Nos. 4,374,780; 4,353,883; 4,348,367; and 5,925,784). Organic phosphinic acids are also known to be useful for extraction of other metals, such as rare earth metals, actinides, and platinum group metals.

Organic mono- and dithio-phosphinic acids have also been found to be useful as metal extractants (see for example U.S. Pat. Nos. 5,028,403 and 4,721,605). The acidity of these phosphorus-containing acids increases with increasing sulfur content, which tends to increase the ability of the acid to extract metals from solutions having low pH but also tends to increase the difficulty of subsequently stripping the metal therefrom.

Thus, it can be appreciated that compounds of formula (I) may be used as metal extractants (e.g. for the recovery of a variety of metals from aqueous solutions containing such metals alone or in combination with other less desirable metals). In embodiments, compounds of formula (I) may be used in cobalt extraction processes.

Bis(2,4,4-trimethylpentyl)-phosphinic acid (disclosed in U.S. Pat. No. 4,374,780 and marketed by Cytec Industries, Inc. under the name CYANEX® 272 is widely used for separating cobalt and/or nickel from either sulfate or low chloride media. CYANEX® 272 can bind cobalt selectively, while simultaneously rejecting calcium, magnesium, and nickel, which are often present in aqueous cobalt (II)-bearing solutions. CYANEX® 272 is also used for the separation of heavy rare earth metals and the selective separation of iron and zinc from cobalt solutions. However, CYANEX® 272 has certain limitations and drawbacks. In particular, CYANEX® 272 becomes increasingly viscous and difficult to work with when it is loaded with cobalt, and as a result, it is usually loaded to only 70-75% of its maximum theoretical capacity in industrial processes.

In the examples described herein, (2,4,4-trimethylpentyl) (1,1,3,3-tetramethylbutyl)phosphinic acid (which is a compound of formula (I) exemplified herein) has been observed to have a cobalt loading capacity comparable to that of CYANEX® 272, but unlike CYANEX® 272, without becoming overly viscous even at maximum cobalt loading. Therefore, in embodiments, (2,4,4-trimethylpentyl)(1,1,3,3 tetramethylbutyl) phosphinic acid allows for cobalt loading of up to 100% of the theoretical capacity in industrial processes, an improvement over CYANEX® 272 on the order of 25-30%, without encountering viscosity problems. An improved practical cobalt loading capacity and/or reduction in viscosity problems (as has been observed with (2,4,4-trimethylpentyl)(1,1,3,3-tetramethylbutyl)phosphinic acid in the examples described herein) may improve the overall efficiency and productivity in certain applications, such as commercial cobalt (II) extraction processes.

In the examples described herein, (2,4,4-trimethylpentyl)(1,1,3,3-tetramethylbutyl)phosphinic acid has also been observed to be better than CYANEX® 272 at rejecting calcium. In commercial cobalt extraction processes, cobalt is typically recovered by stripping it from an organic phase with sulfuric acid. Co-extraction of calcium is undesirable because it may lead to the formation of gypsum at the interface of the organic phase and water phase during the step of stripping cobalt from the organic phase, and so may interfere with and decrease the productivity of the stripping step. Thus, in embodiments, an improved calcium rejection (as has been observed with (2,4,4-trimethyl-pentyl)(1,1,3,3-tetramethylbutyl)phosphinic acid in the examples described herein) may reduce the amount of calcium that is co-extracted in cobalt extraction processes, which may improve the productivity and efficiency of the cobalt stripping step.

Further, in the examples described herein, (2,4,4-trimethylpentyl)(1,1,3,3-tetramethylbutyl)phosphinic acid has been observed to be more selective for cobalt over nickel than CYANEX® 272.

U.S. Pat. No. 5,925,784 discloses bis(1,1,3,3-tetramethylbutyl)phosphinic acid and teaches that this compound has utility as an agent for separating cobalt and/or nickel. However, certain properties of bis(1,1,3,3-tetramethylbutyl)phosphinic acid limit its industrial utility; for example it is a solid at room temperature and has limited solubility in the aromatic and aliphatic solvents commonly used in the industry for cobalt extraction processes. In contrast, in accordance with the present invention, values of $R^1$ and $R^2$ can be chosen to provide compounds of formula (I) that are liquids at room temperature and/or miscible (preferably in all proportions) with the aromatic and aliphatic solvents used in cobalt extraction.

The compounds of formula (I) can be used for cobalt extraction in accordance with known methods (for example, as described in U.S. Pat. Nos. 5,925,784, 4,353,883, and 4,348,367). For example, (2,4,4-trimethyl-pentyl)(1,1,3,3-tetramethylbutyl)phosphinic acid can be directly substituted for CYANEX® 272, although it may be necessary to modify the process somewhat to accommodate for differences between the chemical and physical properties of these compounds. One skilled in the art can adapt such known methods to incorporate the use of compounds of formula (I) using routine experimentation, without the exercise of inventive skill.

All publications and patent applications cited in this specification are herein incorporated by reference as if each individual publication or patent application were specifically and individually indicated to be incorporated by reference.

The citation of any publication is for its disclosure prior to the filing date and should not be construed as an admission that the present invention is not entitled to antedate such publication by virtue of prior invention.

EXAMPLES

Example 1

Synthesis of (2,4,4-trimethylpentyl)(1,1,3,3-tetramethylbutyl)phosphinic acid

The end product of this second synthesis of (2,4,4-trimethylpentyl)(1,1,3,3-tetramethylbutyl)phosphinic acid is referred to hereafter as "Batch 1".

(I) Synthesis of (2,4,4-trimethylpentyl)(1,1,3,3-tetramethylbutyl)phosphine 2,4,4-trimethylpentylphosphine (302.7 g, 99% GC, 2.07 mol, 1.0 eq.), diisobutylene (a mixture of 2,4,4-trimethyl-pentene-1 and 2,4,4-trimethyl-pentene-2; 348.3 g, 3.11 mol, 1.5 eq.) and diethyleneglycol (295 g, weight ratio ~0.97) were added into a three neck flask under nitrogen. The mixture was heated to 80° C. at which time methanesulfonic acid (298.9 g, 3.11 mol, 1.5 eq.) was slowly dripped into the flask through an addition funnel over 50 minutes. The mixture was further heated to reflux at 120° C. and digested overnight (16 hrs.).

The reaction mixture was cooled and toluene (300 ml) was added followed by slow addition of an aqueous solution of NaOH (125 g in 500 g water, 3.11 mol, 1.5 eq.) such that the temperature of the reaction remained below 60° C. After vigorous mixing the contents were transferred to a separatory funnel to allow a clear phase separation. The organic phase was then collected and the solvent and un-reacted starting materials were stripped off under vacuum at 80° C. The resulting product (452 g, 85% yield) was a clear colourless liquid and was analyzed by $^{31}P$ NMR and GC. Results: $^{31}P$ NMR: -23.54 (doublet); and GC/MS: retention time (m/e) 12.70 min (258).

(II) Synthesis of (2,4,4-trimethylpentyl)(1,1,3,3-tetra methylbutyl)phosphinic acid Water (500 g, 1.0 weight ratio relative to volume of dialkylphosphine) was added to a three-necked round bottom flask with a catalytic amount of sulfuric acid (5 g, 1% relative to weight of water). The flask was blanketed with nitrogen and fitted with a mechanical stirring device. The (2,4,4-trimethylpentyl)(1,1,3,3-tetramethylbutyl)phosphine (443 g, 1.7 mol, 1.0 eq.; from step (I) above) was added to the reaction vessel to form a biphasic system, in which the top layer is the organic phase. The reaction mixture was then heated to 50° C. under stirring and nitrogen. The heat source was removed and an aqueous solution of ~25% hydrogen peroxide (700 g, 5.2 mol, 3.0 eq.) was slowly dripped into the reaction mixture ensuring that a slow and steady increase in temperature occurred while avoiding large and sudden temperature changes. After one equivalent of $H_2O_2$ was added (~50 min), the external heat source was applied to provide a reaction temperature of ≥95° C. before the second equivalent of $H_2O_2$ was added, in like fashion (~45 min). At this point the excess $H_2O_2$ was added to ensure complete oxidation of starting material. The reaction mixture was digested at ≥95° C. overnight (16 hrs.) at which time a sample was extracted for $^{31}P$ NMR analysis, to determine the completion of the reaction. Results: $^{31}P$ NMR peak: 63.53.

Upon completion of the reaction, toluene (~200 ml) was added to the mixture to reduce the viscosity of the organic layer. The organic phase was then washed with an equal volume of water. The organic phase was then washed further with an aqueous solution of NaOH (100 g in 1 L of water) to achieve a pH ~7-8. The aqueous layer was removed and the phosphinic acid was restored with an acidic wash ($H_2SO_4$ in water, 10 g/L). The desired product was then stripped of water and dried under vacuum at 80° C. to afford a clear colourless liquid (405 g, 82% yield).

Example 2

Synthesis of (2,4,4-trimethylpentyl)(1,1,3,3-tetramethylbutyl)phosphinic acid

The end product of this second synthesis of (2,4,4-trimethylpentyl)(1,1,3,3-tetramethylbutyl)phosphinic acid is referred to hereafter as "Batch 2".

(I) Synthesis of (2,4,4-trimethylpentyl)(1,1,3,3-tetra methylbutyl)phosphine 2,4,4-trimethylpentylphosphine (412.4 g, 2.82 mol, 1.0 eq.), diisobutylene (a mixture of 2,4,4-trimethyl-pentene-1 and 2,4,4-trimethyl-pentene-2; 474.3 g, 4.23 mol, 1.5 eq.) and diethyleneglycol (413.3 g, weight ratio ~1.00) were added into a three neck flask under nitrogen. The mixture was heated to 80° C. at which time methanesulfonic acid (407.6 g, 4.24 mol, 1.5 eq.) was slowly dripped into the flask through an addition funnel over 50 minutes. The mixture was further heated to reflux at 113° C. overnight (16 hrs.).

The reaction mixture was cooled down and toluene (400 ml) was added followed by slow addition of an aqueous solution of NaOH (174.8 g in 500 g water, 4.37 mol, 1.5 eq.) such that the temperature of the reaction remained below 60° C. After vigorous mixing the contents were transferred to a reparatory funnel with an additional 500 ml water and 300 ml toluene. Clear phase separation was observed and the aqueous layer was removed, followed by an additional wash of the organic layer with 1 L of water. The organic phase was then collected and the solvent and unreacted starting materials were stripped off under vacuum at 80° C. The resulting product (562.1 g, 77% yield) was a clear colourless liquid and was analyzed by $^{31}P$ NMR and GC. Results: $^{31}P$ NMR: −24.76 (doublet); and GC/MS: retention time (m/e) 14.98 min (258).

(II) Synthesis of (2,4,4-trimethylpentyl)(1,1,3,3-tetra methylbutyl)phosphinic acid Water (578 g, ~1.0 weight ratio relative to volume of dialkylphosphine) was added to a three-necked round bottom flask with a catalytic amount of sulfuric acid (5.8 g, 1% relative to weight of water). The flask was blanketed with nitrogen and fitted with a mechanical stirring device. The (2,4,4-trimethylpentyl)(1,1,3,3-tetramethylbutyl)phosphine (556.9 g, 2.16 mol, 1.0 eq.; from step (I) above) was added to the reaction vessel to form a biphasic system, in which the top layer is the organic phase. The reaction mixture was then heated to 50° C. under stirring and nitrogen. The heat source was removed and an aqueous solution of ~25% hydrogen peroxide (889.8 g, 6.54 mol, 3.0 eq.) was slowly dripped into the reaction mixture ensuring that a slow and steady increase in temperature occurred while avoiding large and sudden temperature changes. After one equivalent of $H_2O_2$ was added (~120 min), the external heat source was returned to ensure a reaction temperature of ≥95° C. before the second equivalent of $H_2O_2$ was added, in like fashion (~90 min). At this point the excess $H_2O_2$ was added to ensure complete oxidation of starting material. The reaction mixture was digested at ≥95° C. overnight (16 hrs.) at which time a sample was extracted for $^{31}P$ NMR analysis, to determine the completion of the reaction. Results: $^{31}P$ NMR peak: 63.52.

Upon completion of the reaction, toluene (~500 ml) was added to the mixture to reduce the viscosity of the organic layer. The aqueous phase was removed and the organic was treated with an aqueous solution of NaOH (100 g in 1 L of water) to achieve a pH ~7-8. The aqueous layer was removed and the phosphinic acid was restored with an acidic wash ($H_2SO_4$ in water, 100 g/L). The desired product was then stripped of water and dried under vacuum at 80° C. to afford a clear colourless viscous liquid (551.7 g, 88% yield). A sample was taken for NMR analysis and methylated for analysis by GC/MS. Results: $^{31}P$ NMR peak: 65.73; and GC/MS: retention time (m/e) 19.02 min (272).

Example 3

Two samples of the novel extractant, (2,4,4-trimethylpentyl)(1,1,3,3-tetramethylbutyl)phosphinic acid (Batch 1 and Batch 2) were examined by gas chromatography/mass spectroscopy detector (GC/MSD) to fully characterize the active ingredient, as well as all other minor components and impurities. The acidic components were first converted to their respective methyl esters to allow for elution from the gas chromatograph column.

1. Experimental

Two samples of (2,4,4-trimethylpentyl)(1,1,3,3-tetramethylbutyl)phosphinic acid (Batch 1 and Batch 2) were accurately weighed to the nearest 0.1 milligram and diluted with toluene to a final concentration of 20% by weight. A 500 µL aliquot of the solution was allowed to react with an equal volume of methylating reagent (N,N-dimethylformamide dimethyl acetal), and 0.2 µL of the resulting mixture was injected into the gas chromatograph.

2. Results

The results of GC/MSD analysis (area %) for each component of the 2 samples of (2,4,4-trimethylpentyl)(1,1,3,3-tetramethylbutyl)phosphinic acid (Batch 1 and Batch 2) are shown in Table 1.

TABLE 1

Composition (2,4,4-trimethylpentyl) (1,1,3,3-tetramethylbutyl) phosphinic acid (Batch 1 and Batch 2)

| Retention Time of Methyl Derivatives (min) | Parent Component Corresponding to Eluted Peak | Area % of Total Batch 1 | Batch 2 |
|---|---|---|---|
| | Major Active Component (RR'P(O)OH): | | |
| 16.98 | (1,1,3,3-tetramethylbutyl) (2,4,4-trimethylpentyl) Phosphinic Acid | 82.4 | 85.7 |
| | Minor Active Component Impurities (RR'P(O)OH): | | |
| 17.17 | Bis (2,4,4-trimethylpentyl) Phosphinic Acid | 0.6 | 1.7 |
| 17.26 | Bis (1,1,3,3-tetramethylbutyl) Phosphinic Acid | 1.0 | 1.3 |
| | Total | 1.6 | 3.0 |
| | Monoalkyl Phosphonic Acid Impurities (RP(O)(OH)$_2$): | | |
| 10.92 | (1,1,3,3-tetramethylbutyl) Phosphonic Acid | 0.2 | 0.6 |

TABLE 1-continued

Composition (2,4,4-trimethylpentyl) (1,1,3,3-tetramethylbutyl) phosphinic acid (Batch 1 and Batch 2)

| Retention Time of Methyl Derivatives (min) | Parent Component Corresponding to Eluted Peak | Area % of Total Batch 1 | Area % of Total Batch 2 |
|---|---|---|---|
| 11.21 | (2,4,4-trimethylpentyl) Phosphonic Acid | 0.4 | 0.8 |
| | Total | 0.6 | 1.4 |
| | Trialkyl Phosphine Oxide Impurities ($R_3P(O)$): | | |
| 21.21 | Di(2,4,4-trimethylpentyl) (1,1,3,3-tetramethylbutyl) Phosphine Oxide | 0.0 | 0.8 |
| 21.33 | Di(2,4,4-trimethylpentyl) (1,1,3,3-tetramethylbutyl) Phosphine Oxide, isomer | 0.0 | 0.3 |
| 22.08 | Di(1,1,3,3-tetramethylbutyl) (2,4,4-trimethylpentyl) Phosphine Oxide | 10.6 | 5.0 |
| | Total | 10.6 | 6.1 |
| 10.43 23.92 | Other | 4.6 | 3.8 |

3. Discussion

The chromatographs for the two samples of (2,4,4-trimethylpentyl)(1,1,3,3-tetramethylbutyl)phosphinic acid (Batch 1 and Batch 2) were similar in the composition of components and impurities present and slightly different in the terms of the quantities of components. Besides the major component ((2,4,4-trimethylpentyl)(1,1,3,3-tetramethylbutyl)phosphinic acid), the analysis indicated the presence of the corresponding impurities namely the dialkyl phosphinic acids, the monoalkyl phosphonic acids and the phosphine oxides. The presence of the monoalkyl phosphonic acids must be minimized as they tend to reduce the cobalt/nickel selectivity of the extractant.

Example 4

Characterization of 2,4,4-trimethylpentyl(1,1,3,3-tetramethylbutyl)phosphinic acid The following test work involved studying the performance of the new extractant (2,4,4-trimethyl-pentyl)(1,1,3,3-tetramethylbutyl)phosphinic acid (TEST 1) and CYANEX 272. The experiments examined the extraction of single metals from sulfate solutions and their mutual selectivity as a function of pH, loading capacity of cobalt and viscosity of organic solutions as a function of cobalt loading.

Part A—Extraction from Single Metal Sulfate Solutions at Varying pH

A.1 Experimental

The single metal aqueous solutions were prepared by dissolving a weighed amount of the respective sulfate salt and a weighed amount of sodium sulfate salt in deionized water. The metal concentration in each solution was 0.001M, except Fe(III) which was 0.0015M. The sodium sulfate concentration was 0.5M for all solutions. The metals studied were Co(II), Ni(II), Ca(II), Mg(II), Mn(II), Zn(II), Fe(III), and Cu(II).

The organic solutions were prepared by diluting (2,4,4-trimethylpentyl)(1,1,3,3-tetramethylbutyl)phosphinic acid or CYANEX 272 to 0.1M of phosphinic acid with ISOPAR M diluent. ISOPAR M is an aliphatic (>99.5%) hydrocarbon diluent commercially available from Imperial Oil, Canada.

Equilibrium distributions of the various metals between organic and aqueous phases as a function of pH were determined at 50° C. by contacting equal volumes (300 mL) of the two phases in a jacketed beaker and mixed with mechanical stirring. The temperature of the solution during extraction was maintained at 50° C. by a circulating bath. The pH was adjusted by adding a known volume of either sodium hydroxide or sulfuric acid to the aqueous phase. A contact time of 15 minutes was used between each pH adjustment. Samples of each phase were withdrawn (15 mL) and analysed.

The equilibrium pH of the aqueous raffinate samples was measured using a ROSS combination pH electrode calibrated at room temperature with pH 1.00 (potassium chloride—hydrochloric acid buffer), 4.00 (potassium biphthlate buffer), and 7.00 (potassium phosphate monobasic—sodium hydroxide buffer) buffer solutions.

For all experiments, the aqueous samples were analysed by Atomic Absorption Spectroscopy (AAS). The metal concentration in the organic phase for each sample was deduced by subtracting the raffinate concentration from the initial metal concentration in the feed solution.

A.2 Results

Besides cobalt, nickel and calcium, other metals (i.e. zinc, iron, copper, magnesium and manganese) were also studied. There was however no significant difference between (2,4,4-trimethylpentyl)(1,1,3,3-tetramethylbutyl)phosphinic acid and CYANEX 272 for these metals and their numerical data are therefore not reported here. The numerical data for the extraction of cobalt, calcium and nickel as a function of pH using (2,4,4-trimethylpentyl)(1,1,3,3-tetramethylbutyl) phosphinic acid and CYANEX 272 are shown in Table 2. Table 3 shows the $pH_{50}$ values for each metal using (2,4,4-trimethylpentyl)(1,1,3,3-tetramethylbutyl)phosphinic acid ("TEST") and CYANEX 272 as well as the $\Delta pH_{50}$ ($\Delta pH_{50}=pH_{50}Co-pH_{50}metals$) values, respectively. The $pH_{50}$ values were determined using the log of the distribution ratio, log D, and plotting the values as a function of pH. The distribution coefficient, D, is defined as the ratio of the total metal content in the organic phase to the metal content in the aqueous phase.

The results indicate selectivity for cobalt-nickel, cobalt-zinc, cobalt-iron, and cobalt-calcium for (2,4,4-trimethylpentyl)(1,1,3,3-tetramethylbutyl)phosphinic acid. Furthermore, (2,4,4-trimethylpentyl)(1,1,3,3-tetramethylbutyl)phosphinic acid shows a substantial increase in selectivity over CYANEX 272 for cobalt over both calcium and nickel. This higher cobalt-calcium selectivity could have a great advantage in a solvent extraction plant by decreasing the formation of gypsum in the circuit.

TABLE 2

Extraction of cobalt, nickel and calcium with CYANEX 272 and (2,4,4-trimethylpentyl)(1,1,3,3-tetramethylbutyl) phosphinic acid

| Co | | Ni | | Ca | |
|---|---|---|---|---|---|
| pH | % E | pH | % E | pH | % E |
| (2,4,4-trimethylpentyl)(1,1,3,3-tetramethylbutyl) phosphinic acid | | | | | |
| 3.49 | 0.0 | 6.45 | 0.0 | 5.37 | 5.4 |
| 4.29 | 22.6 | 6.69 | 9.1 | 5.79 | 12.8 |
| 4.81 | 63.3 | 6.85 | 22.3 | 6.01 | 26.3 |
| 5.11 | 82.5 | 7.02 | 38.7 | 6.47 | 48.2 |
| 5.75 | 97.2 | 7.28 | 63.3 | 6.74 | 75.2 |
| 6.38 | 99.6 | 7.51 | 78.9 | 7.05 | 96.2 |
| 6.61 | 99.8 | 7.74 | 91.9 | 7.33 | 100.0 |
| | | 7.98 | 96.5 | | |

TABLE 2-continued

Extraction of cobalt, nickel and calcium with CYANEX 272 and (2,4,4-trimethylpentyl)(1,1,3,3-tetramethylbutyl) phosphinic acid

| Co | | Ni | | Ca | |
|---|---|---|---|---|---|
| pH | % E | pH | % E | pH | % E |
| CYANEX 272 | | | | | |
| 3.62 | 0.3 | 4.37 | 0.0 | 4.40 | 0.0 |
| 3.99 | 6.6 | 6.09 | 11.6 | 5.23 | 22.4 |
| 4.18 | 21.5 | 6.24 | 19.0 | 5.79 | 55.8 |
| 4.53 | 49.4 | 6.51 | 38.3 | 6.28 | 87.5 |
| 4.85 | 79.6 | 6.93 | 76.0 | 6.70 | 96.8 |
| 5.17 | 94.0 | 7.11 | 85.6 | 6.95 | 98.4 |
| 5.63 | 98.8 | 7.32 | 92.7 | 7.32 | 99.4 |
|  |  | 7.54 | 96.3 |  |  |

TABLE 3

$pH_{50}$ and $\Delta pH_{50}$ ($\Delta pH_{50} = pH_{50}Co - pH_{50}$metals) values for each metal using (2,4,4-trimethylpentyl)(1,3,3-tetramethylbutyl) phosphinic acid ("TEST") and CYANEX 272

| Extractant | Conc. (M) | $pH_{50}$ Co(II) | $pH_{50}$ Ni(II) | $pH_{50}$ Ca(II) | $\Delta pH_{50} =$ $pH_{50}Co - pH_{50}$metals Co(II) | Ni(II) | Ca(II) |
|---|---|---|---|---|---|---|---|
| TEST | 0.1 | 4.65 | 7.20 | 6.49 | — | −2.55 | −1.84 |
| CYANEX 272 | 0.1 | 4.51 | 6.69 | 5.66 | — | −2.18 | −1.15 |

Part B—Cobalt Loading Capacity and Viscosity

B.1 Experimental for the Loading Capacity of Cobalt

The aqueous solution was prepared by dissolving a weighed amount of cobalt sulfate salt in deionized water. The metal concentration in the solution was 40 g/L. The organic solutions were prepared by diluting (2,4,4-tri-methylpentyl)(1,1,3,3-tetramethylbutyl)phosphinic acid extractant or CYANEX 272 to 0.14M of phosphinic acid with ISOPAR M diluent. ISOPAR M is an aliphatic (>99.5%) hydrocarbon diluent commercially available from Imperial Oil, Canada.

Equilibrium distributions of cobalt between the organic and aqueous phases was determined at 50° C. by contacting an aqueous volume (250 mL) and an organic volume (50 mL) to give an aqueous to organic phase ratio of 5. The two phases were contacted in a jacketed beaker and mixed with mechanical stirring. The temperature of the solution during the extraction was maintained at 50° C. by a circulating bath. The pH was adjusted by adding a known volume of sodium hydroxide to the aqueous phase. A constant pH of 6.13±0.03 for a period of 15 minutes was necessary to ensure maximum loading of the metal. The phases were separated and the organic filtered through phase separating (P/S) paper to ensure that no entrained aqueous was present. The metal concentration in the organic was determined by stripping with 100 g/L $H_2SO_4$ using equal volumes of both phases (40 mL) for 5 minutes at room temperature. The strip liquor was collected in a sample vial. An aliquot (35 mL) of the stripped organic was stripped a second time with an equal volume (35 mL) of fresh acid. This was repeated a third time using 30 mL of stripped organic and 30 mL of fresh acid.

The three strip liquors were kept separate and analysed individually by ICP. The three strip liquor concentrations were summed to determine the amount of cobalt loaded. A total of three loading tests were completed (TEST 1, TEST 2, and TEST 3).

The equilibrium pH of the aqueous samples was measured as previously described in section above.

B.2 Experimental for the Viscosity of Organic Solutions as a Function of Cobalt Loading The aqueous solution was prepared by dissolving a weighed amount of cobalt sulfate salt in deionized water. The metal concentration in the solution was 40 g/L.

The organic solutions were prepared by diluting a weighed amount of either CYANEX 272 (200 grams, Lot #WE2060451) or (2,4,4-trimethylpentyl)(1,1,3,3-tetramethyl-butyl)phosphinic acid extractant (200 grams, TEST 3) extractant to 20% (w/w) with ISOPAR M diluent. These solutions were split in two equal portions in order to prepare the different per cent cobalt loading.

Equilibrium distributions of cobalt between the organic and aqueous phases were determined as previously described in the section above with the exceptions that the temperature was room temperature and the aqueous to organic phase ratio was of unity (500 mL volume for each phase). A constant pH of 5.90±0.02, and pH of 6.05±0.02 for CYANEX 272 and (2,4,4-trimethylpentyl)(1,1,3,3-tetramethyl-butyl)phosphinic acid extractant (TEST 3), respectively, for a period of 15 minutes was necessary to ensure maximum loading of the metal. Phases were separated and the organic was centrifuged for 30 minutes at 3000 rpm to ensure that no entrained aqueous or precipitate was present.

Samples were next prepared by mixing 100% loaded and 0% loaded at various volumes such that viscosities of 0%, 10%, 30%, 45%, 60%, 75%, 90%, and 100% cobalt loading could be measured at varying temperatures.

The samples were tested using a TA Instruments' AR1000N rheometer. A step flow method was used in 90 second intervals ranging 10 to 60° C. In most cases data points were collected at least every 10° C. Temperature control (+/−0.1° C.) was provided by a Peltier plate. The geometry consisted of a 60 mm cone and plate with a 2° angle. All samples were found to be Newtonian, i.e., their viscosities are independent of the shear rate. Thus tests with varying temperatures reported were all done at the same shear rate (500/s).

B.3 Results

The calculated cobalt concentration in the organic phase was determined for three samples of (2,4,4-trimethyl-pentyl)(1,1,3,3-tetramethylbutyl)phosphinic acid (TEST 1, TEST 2, and TEST 3) and CYANEX 272 and is shown in Table 4.

TABLE 4

Loading capacity of cobalt with CYANEX 272 and (2,4,4-trimethylpentyl) (1,1,3,3-tetramethylbutyl)phosphinic acid (TEST 1, TEST 2, and TEST 3)

|  | Organic Conc. (M) | Cobalt Concentration in Organic (g/L) | Cobalt Concentration in Organic (M) | Ratio Org Conc./Co Conc. in Org |
|---|---|---|---|---|
| TEST 1 | 0.145 | 3.65 | 0.0619 | 2.34 |
| TEST 2 | 0.145 | 3.66 | 0.0621 | 2.33 |
| TEST 3 | 0.145 | 3.65 | 0.0619 | 2.34 |
| CYANEX 272 | 0.138 | 3.85 | 0.0653 | 2.11 |

The results indicate a slight difference in the loading capacity of the two extractants with CYANEX 272 having a slightly higher maximum cobalt loading capacity than (2,4,4-trimethylpentyl)(1,1,3,3-tetramethylbutyl)phosphinic acid.

The following two tables (5 and 6) show the viscosity of both (2,4,4-trimethylpentyl)(1,1,3,3-tetra-methylbutyl)phosphinic acid and CYANEX 272. Results indicate that the viscosity does not change much with varying cobalt solution loadings for (2,4,4-trimethylpentyl)(1,1,3,3-tetramethylbutyl)phosphinic acid. On the other hand, there is a large increase in viscosity between 75, 90, and 100% cobalt solution loading for the CYANEX 272 samples. On a practical basis, this means that 100% cobalt loading can be achieved with (2,4,4-trimethylpentyl)(1,1,3,3-tetra-methylbutyl)phosphinic acid whereas CYANEX 272 is limited to 70-75% cobalt loading to limit the viscosity issues.

TABLE 5

Viscosity of CYANEX 272 at various cobalt loading

| Temp. (° C.) | Cobalt loading | | | | | | | |
|---|---|---|---|---|---|---|---|---|
| | 0% | 10% | 30% | 45% | 60% | 75% | 90% | 100% |
| | Viscosity (Centipoise) | | | | | | | |
| 10 | 5.5 | 5.832 | 5.959 | 6.222 | 6.732 | 7.1 | 60.5 | 298.7 |
| 15 | 4.6 | | 4.985 | 5.217 | 5.621 | | 47.3 | |
| 20 | 3.92 | 4.167 | 4.247 | 4.434 | 4.764 | 5.12 | 37.4 | 193 |
| 25 | 3.37 | 3.603 | 3.643 | 3.811 | 4.091 | | 29.9 | |
| 30 | 2.94 | 3.156 | 3.178 | 3.313 | 3.547 | 3.78 | 24.3 | 123.7 |
| 40 | 2.31 | 2.463 | 2.48 | 2.566 | 2.748 | 2.86 | 16.5 | 76.82 |
| 50 | 1.87 | | | 2.071 | 2.188 | 2.33 | 11.5 | 50.67 |
| 60 | 1.58 | 1.637 | 1.667 | 1.739 | 1.832 | 1.95 | 8.26 | 34.46 |

TABLE 6

Viscosity of (2,4,4-trimethylpentyl) (1,1,3,3-tetramethylbutyl) phosphinic acid at various cobalt loading

| Temp. (° C.) | Cobalt loading | | | | | | | |
|---|---|---|---|---|---|---|---|---|
| | 0% | 10% | 30% | 45% | 60% | 75% | 90% | 100% |
| | Viscosity (Centipoise) | | | | | | | |
| 10 | 5.96 | 6.73 | 6.73 | 6.9 | 6.95 | 7.07 | 7.34 | 8.02 |
| 15 | 4.94 | 5.586 | 5.55 | 5.71 | 5.75 | 5.82 | 6.04 | |
| 20 | 4.18 | 4.73 | 4.67 | 4.79 | 4.83 | 4.88 | 5.07 | 5.64 |
| 25 | 3.57 | 4.05 | 3.99 | 4.08 | 4.12 | 4.16 | 4.31 | |
| 30 | 3.1 | 3.5 | 3.43 | 3.52 | 3.54 | 3.59 | 3.69 | 4.08 |
| 40 | 2.38 | 2.68 | 2.63 | 2.70 | 2.7 | 2.74 | 2.8 | 3.03 |
| 50 | 1.91 | | | 2.14 | 2.15 | 2.14 | 2.22 | 2.40 |
| 60 | 1.57 | 1.76 | 1.74 | 1.79 | 1.77 | 1.76 | 1.82 | 2.00 |

What is claimed is:

1. A method for preparing a compound of Formula (I):

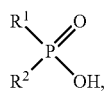

and salts thereof, wherein:
$R^1$ and $R^2$ are different and each of $R^1$ and $R^2$ is a hydrocarbyl group containing a total of from 5 to 16 carbon atoms, wherein said hydrocarbyl group is chosen from
(i) —$CH_2$—$CHR^3R^4$ where $R^3$ is methyl or ethyl and $R^4$ is alkyl; or
—$CR^3(CH_2R^5)R^6$ where $R^3$ is methyl or ethyl; $R^5$ is H or alkyl; $R^6$ is alkyl; or $R^5$ and $R^6$ and the carbon atoms to which they are bonded form a five or six-membered cycloalkyl ring;
the method comprising:
allowing a secondary phosphine to react with
an oxidizing agent to produce a corresponding phosphinic acid.

2. A method according to claim 1, wherein the compound of Formula (I) is a phosphinic acid and the oxidizing agent is hydrogen peroxide.

3. A method according to claim 1, wherein said compound according to Formula (I) contains a total of between 12 and 20 carbon atoms.

4. A method according to claim 1, wherein each of $R^1$ and $R^2$ is independently chosen from a $C_6$-$C_{16}$ alkyl.

5. A method according to claim 4, wherein each of $R^1$ and $R^2$ is independently chosen from a $C_8$ alkyl.

6. A method according to claim 5, wherein each of $R^1$ and $R^2$ is independently selected from 2,4,4-trimethylpentyl; 1,1,3,3-tetramethyl-butyl; 2-ethylhexyl; and 1-methyl-1-ethylpentyl.

7. A method according to claim 6, wherein the compound according to Formula (I) is selected from the group consisting of
(2,4,4-trimethylpentyl)(1,1,3,3-tetramethylbutyl)phosphinic acid:

(1,1,3,3-tetramethylbutyl)(2-ethyl-hexyl)phosphinic acid;
(2,4,4-trimethylpentyl)(2-ethylhexyl)phosphinic acid;
(2,4,4-trimethylpentyl)(1-methyl-1-ethylpentyl)phosphinic acid; and
(1-methyl-1-ethylpentyl)(2-ethyl-hexyl)phosphinic acid.

8. A method according to claim 7, wherein the compound according to Formula (I) is (2,4,4-trimethylpentyl)(1,1,3,3-tetramethylbutyl)phosphinic acid.

9. A method according to claim 1, wherein the secondary phosphine is selected from the group consisting of (2,4,4-trimethylpentyl)(1,1,3,3-tetramethylbutyl)phosphine; (1,1,3,3-tetramethylbutyl)(2-ethyl-hexyl)phosphine; (2,4,4-trimethylpentyl)(2-ethylhexyl)phosphine; and (2,4,4-trimethylpentyl)(1-methyl-1-ethylpentyl)phosphine.

* * * * *